US005466458A

United States Patent [19]

Martin et al.

[11] Patent Number: 5,466,458

[45] Date of Patent: Nov. 14, 1995

[54] EMULSIFIED SPRAY FORMULATIONS

[75] Inventors: Robert Martin; George R. Cayley, both of Hertfordshire, England; Jonathan R. M. Thacker, Paisley, Scotland; Franklin R. Hall, Wooster, Ohio; Denise K. North, Hertfordshire, England; John M. Groome, Hertfordshire, England; David A. Jeffries, Hertfordshire, England

[73] Assignee: Roussel Uclaf, France

[21] Appl. No.: 196,809

[22] Filed: Feb. 15, 1994

Related U.S. Application Data

[63] Continuation-in-part of Ser. No. 979,452, Nov. 20, 1992, abandoned, and Ser. No. 78,212, Jun. 17, 1993, abandoned, said Ser. No. 979,452, is a continuation of Ser. No. 845,804, Mar. 9, 1992, abandoned, which is a continuation of Ser. No. 438,399, Dec. 27, 1989, abandoned.

[51] Int. Cl.[6] .................... A01N 25/00

[52] U.S. Cl. .................... 424/405; 424/DIG. 8; 424/DIG. 10

[58] Field of Search .................... 424/405; 514/558, 514/389, 242, 86

[56] References Cited

U.S. PATENT DOCUMENTS

| | | | |
|---|---|---|---|
| 3,931,413 | 1/1976 | Frick et al. | 514/558 |
| 4,176,189 | 11/1979 | Itaya et al. | 514/389 |
| 4,308,258 | 12/1981 | Okabe et al. | 514/86 |
| 4,327,094 | 4/1982 | Mizutani et al. | 514/242 |
| 4,647,610 | 3/1987 | Sperry et al. | 524/377 |

FOREIGN PATENT DOCUMENTS

| | | |
|---|---|---|
| 0210747 | 2/1987 | European Pat. Off. . |
| 0331474 | 9/1989 | European Pat. Off. . |
| 1297607 | 12/1962 | Germany . |

OTHER PUBLICATIONS

K. Naumann, 1939 "Synthetic Pyrethroid Insecticides: Structures and properties" Springer–Verlag pp. 96–99.
"Kolos" Protection of Plants, No. 6, 1980, Ways of Increasing the Effectiveness of Pesticides.

*Primary Examiner*—Thurman K. Page
*Assistant Examiner*—William E. Benston, Jr.
*Attorney, Agent, or Firm*—Nixon & Vanderhye

[57] ABSTRACT

A formulation suitable for spraying or for dilution with water to form a sprayable preparation, the formulation comprising an active ingredient, optionally a carrier or solvent for the active ingredient, an emulsifier and an evaporation retardant where the formulation satisfies the following formula $$\frac{\text{mass of oil phase}}{\text{mass of retardant}} \leq \frac{M_{oil}}{M_{retardant}} \times \text{Exp}\left[\ln\left(\frac{L}{4}\right) + C\ln(AX^B)\right]$$

where L is less than or equal to 15, A=700376, B=−1.51, C=0.8472, $M_{oil}$ is the weighted average relative molar mass of the oil phase $M_{retardant}$ is the weighted average relative molar mass of the retardant, and X=($M_{oil}$) 1.8/Y, where Y is the molar solubility ratio of the formulation, defined as the minimum number of moles of the oil phase which will dissolve the retardant, divided by the number of moles of retardant, provided that, in the formula above, any solvent which has no liquid phase at 27° C. at atmospheric pressure is extruded. The formulation may include a pesticide or herbicide. The action of the evaporation retardant is improved.

25 Claims, No Drawings

EMULSIFIED SPRAY FORMULATIONS

This application is a continuation-in-part of earlier application Ser. No. 07/979,452 filed Nov. 20, 1992, abandoned, which is a continuation of Ser. No. 07/845,804 filed Mar. 9, 1992, abandoned, which is a continuation of Ser. No. 07/438,399 filed Dec. 27, 1989, abandoned. This application is also a continuation-in-part of application Ser. No. 08/078,212 filed Jun. 17, 1993, abandoned.

The present invention relates to spray formulations, especially pesticidal formulations of the sort which may be diluted with water to form a sprayable preparation, for example a pressure pack ("aerosol") preparation or a spray, particularly an ultra low volume (ULV) spray for domestic, horticultural, agricultural, environmental or industrial use.

Water-based sprays are advantageous because they cost less than oil-based sprays and are often less toxic to mammals. However, particularly then the ambient temperature is high, the water in the spray droplets evaporates and the droplets become smaller and drift more readily from the area being sprayed. The size of the droplets is frequently specially chosen to suit the application, for example to maximise droplet adherence to flying insects or adherence to plant foliage, to increase bio-availability, or to control the size of the area being sprayed and the delivery rate per square metre; such care is pointless if the spray droplets change size, possibly unpredictably, following spraying.

GB-A-2 095 109 discloses improved water-dilutable formulations comprising a long-chain fatty alkanol which retards the evaporation of the water from the drops of the spray.

We have now found that still better evaporation retardation can be achieved if the formulation satisfies the following Formula:

$$\frac{\text{mass of oil phase}}{\text{mass of retardant}} \leq \frac{M_{oil}}{M_{retardant}} \times \text{Exp}\left[\frac{\ln\left(\frac{L}{4}\right) + C\ln(AX^{B})}{C}\right]$$

where L is less than or equal to 15, A: 700376, B=–1.51, C=0.8472, $M_{oil}$ is the weighted average relative molar mass of the oil phase, $M_{retardant}$ is the average molar mass of the retardant, and $$X = \frac{(M_{oil})^{1.8}}{Y}$$

where Y is the molar solubility ratio of the formulation, defined as the minimum number of moles of oil phase which will dissolve the retardant, divided by the number of moles of retardant, provided that, in the Formula above, any solvent which has no liquid phase at 27° C. at atmospheric pressure is excluded.

For the avoidance of doubt, and to clarify any ambiguities which may arise in the printing or copying of this specification, it is to be noted that the relational symbol in the Formula is "less than or equal to", "Exp" means the exponential of what follows in brackets, "1n" means the natural logarithm, i.e. $\log_e$, L is divided by 4, X is raised to the power B, B is a negative value (minus 1.51) and, in the definition of X, $M_{oil}$ is raised to the power 1.8.

The "oil phase" is the liquid non-aqueous phase and will comprise one or more of the active ingredient, the solvent therefor and the emulsifier.

Preferably L, which is related to the evaporation rate from the sprayed droplets, is less than 12, 10, or 8 and is most preferably less than 5. A distilled water spray has an "L" value of about 26, and most conventional diluted formulations have a value of about 22–30. In the formulations of the invention, "L" can be set at a desired value in order to calculate the required ratios of the ingredients. "L" can also be measured for a given formulation by the method described below.

The evaporation retardant may be any film-forming compound, preferably an alkanol. It is preferably a primary alcohol; preferably with no more than one or two side substitutions selected from methyl, ethyl, tri fluoromethyl and halo (e.g. fluoro or chloro), with such substitutions preferably remote from the alcohol group (preferably at least 7 carbon atoms away from the hydroxyl group), and preferably the alkanol is not substituted at all: preferably $C_{16-20}$; preferably saturated; and preferably a solid at 27° Octadecan-1-ol and, particularly, hexadecan-1-ol are preferred. Hexadecan-1-ol (also known as cetyl alcohol) is usually available commercially as a mixture with a minor proportion of octadecan-1-ol (stearyl alcohol) and such "cetostearyl alcohol" is quite satisfactory. Heptadecan-1-ol performs adequately but is much more expensive. Other highly effective film-forming agents include 1-hexadecylamine, 1-heptadecylamine and 1-octadecylamine. Less preferred film-forming agents include hexadecan-2-ol, 1,2-hexadecandiol, methyl stearate, stearyl acetate, methyl palmitate and 1,2-octadecandiol. N-alkoxyalkanols may be used, for example $CH_3(CH_2)_{21}OC_2H_4OH$, $CH_3(CH_2)_{21}OC_3H_6OH$, $CH_3(CH_2)_{17}OC_2H_4OH$ or $CH_3(CH_2)_{15}OC_2H_4OH$, as may oxyethylene-docosanol and mixtures of any of the said evaporation retardants.

The emulsifier may be any suitable compound or mixture of compounds. Cationic emulsifiers can be used, but they tend to irritate the users' eyes. Anionic emulsifiers such as calcium dodecyl benzene sulphate (CDBS) or sodium di-isopropyl naphthalene sulphonate (SDNS) can also be used, but these are not as effective at stabilising the emulsion. Preferably, the emulsifier is a non-ionic compound, or mixture of non-ionic compounds, having an HLB (hydrophilic/lipophilic balance) of 8–18. Suitable compounds include polyoxyethylene stearyl ethers(PSE), polyoxyethylene monolaurates(PEM), polyoxyethylene mono-oleates (PMO), sorbitan mono-oleate (SMO), nonylphenol ethoxylate (NPE), polyethylene glycol (PEG) and blends of oleyl ethoxylate (10 mole) and PEG20 glyceryl oleate (OE/PGO).

These emulsifiers are available as follows:

| Abbrev | Trade name | Supplier |
|---|---|---|
| OE/PGO | Tegoplant EM11 | Th. Goldschmidt Ltd |
| PSE | Brij 72, Brij 76, Brij 78 | ICI Speciality Chemicals |
| PEM | Tween 20 | ICI Speciality Chemicals |
| SMO | Span 80 | ICI Speciality Chemicals |
| PMO | Tween 80 | ICI Speciality Chemicals |
| NPE | Ethylan KEO, 55, BV | Lankro Chemicals Limited |
| CDBS | Arylan CA | Lankro Chemicals Limited |

-continued

| Abbrev | Trade name | Supplier |
|--------|------------|----------|
| SDN | Aerosol OS | Cyanamid GB Ltd |

The solvent, at least for an oil-soluble active ingredient, preferably has a low relative molecular mass, namely less than about 200. Suitable compounds include lower alkyl esters, lower ketones, lower alkanols and lower alkanes, the term "lower" meaning $C_{1-10}$, preferably $C_{1-8}$.

Particular solvents include the following, all available from Exxon Chemicals Limited.

"Solvesso 150"—An aromatic hydrocarbon solvent (C9 to C11) with a distillation range 190° to 210° C.

"Solvesso 200"—An aromatic hydrocarbon solvent (C10 to C12) with a distillation range 226° to 290° C.

"Exxate 700"—Heptyl acetate 99% pure, or Odourless kerosene—A mixture of high boiling non-aromatic hydrocarbons consisting of paraffins and naphthenes with a distillation range of 180° to 270° C.

The formulation may comprise more than one active ingredient (optionally with a synergist or potentiator, which is regarded as an active ingredient for the purpose of the Formula above), more than one solvent, more than one emulsifier and/or more than one retardant, together with other ingredients such as perfumes, dyes, anti-foam agents, solids (especially to form wettable powders) and thickeners. Some compounds, such as butane, propane and dichlorodifluoromethane and carbon dioxide are highly volatile and are used as propellants in pressure pack formations. Although sometimes acting as solvents for particular active ingredient, they almost instantly evaporate from the drops when sprayed and are thus excluded from the calculations in the Formula above. Such solvent/propellants are those which have no liquid phase at 27° C. at atmospheric pressure.

$M_{oil}$ the average molecular weight of the oil phase, is the weighted average, i.e. taking into account the relative proportions of the ingredients.

The value "Y", namely the molar solubility ratio of the formulation, may be derived empirically by making up at 40° C. a series of mixtures with different ratios of oil phase to alkanol, allowing the mixtures to cool to 27° C., leaving the cool mixtures for at least 48 hours at 27° C., and determining the amount, in moles, of the oil phase which is needed to dissolve completely a given amount of retardant, in moles. The former is then divided by the latter to give Y.

The formulations of the invention may be (i) single phase substantially anhydrous formulations, or (ii) emulsions comprising water. In a formulation of type (ii), some of the active ingredient, solvent or emulsifier components may partition into the aqueous phase, in which case such components are deemed not to be part of the oil phase in the Formula above. Examples of water-miscible solvents include ethanol, propanol, ethylene glycol and propylene glycol. It has been found that partially water-miscible components may be treated as being wholly water-miscible and hence excluded from the oil phase in the calculations.

When the formulation of the invention is diluted to give a sprayable preparation, the molar ratio of water to retardant should preferably not exceed about 9000, and preferably not exceed 8000, 7000 or 6000. It is perfectly possible to prepare a more dilute solution, but all that will happen is that the retardant will be unable to form a film over the entire surface of the droplets, and the water will evaporate until there is a sufficient concentration of the retardant to form a complete film which will then retard further evaporation. Thus, the droplet size is less controllable and, in addition, a larger volume of solution must be stored and pumped, which is inefficient.

The active ingredient may be an insecticide, acaricide, herbicide, fungicide, plant growth regulator, insect behaviour modifier, biological control agent (e.g. viruses, bacteria and eggs of parasites), dye, perfume, bactericide, lubricant, medicament, paint, polish, lacquer (including hair lacquer), textile treatment (including sizes), or any other compound to be sprayed in a water-based formulation. Sprays in accordance with the invention are particularly suitable for spraying buildings, residential or commercial areas and insect breeding grounds (such as swamps and other tracts of water) with insecticide and for spraying crops with herbicides, insecticides, fungicides and plant growth regulators.

Suitable pesticides including pyrethroids (such as permethrin, deltamethrin, cypermethrin (including alpha-methrin, the allethrins, fenvalerate and cyfluthrin), organophosphates (such as ethion, chlorfenvinphos, chlorpyrifos (methyl) or coumaphos), carbamates, organochlorines (such as DDT, dieldrin, dicofol, chlorpropylate or tetradifon), lipid amides, bicyclooctanes and dithianes. Suitable herbicides include glyphosate.

The sprays may be delivered by pumping through a nozzle, especially a sonic nozzle, by pumping over an ultrasonic nebulizer, or via a spinning disc. The droplets may be electro-statically charged, if desired.

As well as the uses discussed above, at least some of the formulations of the invention can be used to form a larvicidal film over a lake.

To determine whether a given formulation satisfies the Formula given above, the following procedure may be adopted. If the formulation is an emulsion, the emulsion should first be "broken" by extraction of the concentrate with a suitable solvent such as ether. The ingredients are then analysed by suitable quantitative and qualitative analytical methods. If not already known, the miscibility of each component with water is tested: if the component is water-miscible in the conditions of the formulation, it is excluded from the calculations. The solubility of the evaporation retardant in the oil phase (excluding water-miscible components) is determined. The parameters are then operated on in the manner defined in the Formula to see whether the (mass of oil phase)/(mass of retardant) ratio is less than or equal to the figure on the right hand side of the Formula. This procedure is explained below with specific reference to the Examples.

Preferred embodiments of the invention will now be described by way of example.

The present invention also relates to a method of controlling the damage caused by phytophagus insects to crops by the application of an anti-evaporant formulation containing an insecticide using the above described spray formulations which have evaporation retardant properties such formulations contain an oil phase, a retardant and an active ingredient, for example a pesticide.

Mite resurgence is a phenomenon encountered when broad spectrum insecticides, such as the pyrethroids, are used to control insects on crops. Treatment with the pyrethroids controls the major pest on the crops, for example caterpillars, but results in an explosion of the mite population which was previously at a low density (mite resurgence). One reason for mite resurgence is that the pyrethroids stimulate the mites to increase their reproductive rate.

The above described spray formulations containing a pyrethroid can be applied to crops without causing mite resurgence.

Accordingly, the present invention also provides a method of controlling insects on plants which comprises the application to the plant of an effective amount of an aqueous formulation that contains a pyrethroid insecticide as active ingredient, an evaporation retardant and an emulsifier that satisfies the formula:

$$\frac{\text{mass of oil phase}}{\text{mass of retardant}} \leq \frac{M_{oil}}{M_{retardant}} \cdot X \operatorname{Exp}\left[[\ln(L/4) + [C \times \ln(AX^B)]]/C\right]$$

where L is less than or equal to 15, A=700376, B=−1.51, C=0.8472, $M_{oil}$ is the weighted average relative molar mass of the oil phase, $M_{retardant}$ is the average molar mass of the retardant, and $$

(S)-α-cyano-3-phenoxybenzyl-(1R,3S)-3-[(Z)-3-[bis (trifluoromethyl)methoxy]-3-oxo-1-propenyl]-2,2-dimethylcyclopropanecarboxylate (acrinathrin), (RS)-α-cyano-3-phenoxybenzyl-(RS)-2-(4-chlorophenyl)-3-methylbutyrate (fenvalerate) and the single (S), (S) isomer (esfenvalerate), (RS)-α-cyano-3-phenoxybenzyl-(S)-2-(4-difluoromethoxyphenyl)-3-methyl butyrate (flucythinate), (RS)-α-cyano-3-phenoxybenzyl-N-(2-chloro-α, α, α-trifluoro-p-tolyl)-D-valinate (fluvalinate), (RS)-α-cyano-4-fluoro-3-phenoxybenzyl-(1RS)-cis-trans-3-(2,2-dichlorovinyl)-2,2-di-methylcyclopropanecarboxylate (cyfluthrin), (RS)-α-cyano-4-fluoro-3-phenoxybenzyl-(1RS)-cis-trans-3-(2-chloro-2(4-chlorophenyl)vinyl)-2,2-dimethylcyclopropanecarboxylate (flumethrin), 2-methylbiphenyl-3-yl-methyl-(Z)-1RS,3RS)-3-(2-chloro-3,3,3-trifluoro-prop-1-enyl)-2,2-dimethylcyclopropanecarboxylate (Bifenthrin); the allethrins, for example (1RS)-3-allyl-2-methyl-4-oxo-cylopent-2-enyl-(1R,3R)-2,2-dimethyl-3-(2-methylprop-1-enyl)-cyclopropanecarboxylate (bioallethrin), (1S) -allyl-2-methyl-4-oxocyclopent-2-enyl-(1R, 3R)-2,2-dimethyl-3-(2-methylprop-1-enyl)cyclopropanecarboxylate (S-bioallethrin), and mixtures of allethrin isomers (esbiothrin); the resmethrins, for example 5-benzyl-3-furylmethyl(IRS, 3RS; IRS, 3SR)-2,2-dimethyl-3-(2-methyl-prop-1-enyl)cyclopropanecarboxylate (resmethrin) and 5-benzyl-3-furylmethyl (1R,3R)-2,2-dimethyl-3-(2-methylprop-1-enyl)cyclopropanecarboxylate (bioresmethrin).

Octadecan-1-ol and, particularly, hexadecan-1-ol are preferred evaporation retardants. Hexadecan-1-ol (also known as cetyl alcohol) is usually available commercially as a mixture with a minor proportion of octadecan-1-ol (stearyl alcohol) and such "cetostearyl alcohol" is quite satisfactory. Heptadecan-1-ol performs adequately but is much more expensive. Other highly effective evaporation retardants include 1-hexadecylamine, 1-heptadecylamine and 1-octadecylamine. Less preferred evaporation retardants include hexadecan-2-ol, 1,2-hexadecandiol, methyl stearate, stearyl acetate, methyl palmirate and 1,2-octadecandiol. N-alkoxyalkanols may be used, for example $CH_3(CH_2)_{21}OC_2H_4OH$, $CH_3(CH_2)_{21}OC_3H_6OH$, $CH_3(CH_2)_{17}OC_2H_4OH$ or $CH_3(CH_2)_{15}OC_2H_4OH$, as may oxyethylene-docosanol and mixtures of any of the said evaporation retardants.

The amount of emulsifier present in the formulation will be less than twice the amount of the evaporation retardent present and will preferably be less than the amount of the evaporation retardant present.

The emulsifier may be any suitable compound or mixture of compounds. Cationic emulsifiers can be used, but they tend to irritate the user's eyes. Artionic emulsifiers such as calcium dodecyl benzenesulphate (CDBS) or sodium d-isopropyl naphthalenesulphonate (SDNS) can also be used, but these are not as effective at stabilising the emulsion whilst maintaining evaporation retarding properties. Preferably, the emulsifier is a non-ionic compound, or mixture of non-ionic compounds, having an HLB (hydrophilic/lipophilic balance) of 6–20 and preferably 8–18. Suitable compounds include polyoxyethylene stearyl ethers (PSE), polyoxyethylene monolaurates (PEM), polyoxyethylene mono-oleates (PMO), sorbitan mono-oleate (SMO), nonylphenol ethoxylate (NPE), polyethylene glycol (PEG) and blends of oleyl ethoxylate (10 mole), and PEG20 glyceryl oleate (OE/PGO).

These emulsifiers are available as follows:

| Abbrev | Trade name | Supplier |
|---|---|---|
| OE/PGO | Tegoplant EM11 | Th. Goldschmidt Ltd. |
| PSE | Brij 72, Brij 76, Brij 78 | ICI Speciality Chemicals |
| PEM | Tween 20 | ICI Speciality Chemicals |
| SMO | Span 80 | ICI Speciality Chemicals |
| PMO | Tween 80 | ICI Speciality Chemicals |
| NPE | Ethylan KEO, 55, BV | Lankro Chemicals Limited |
| CDBS | Arylan CA | Lankro Chemicals Limited |
| SDN | Aerosol OS | Cyanamid GB Ltd. |

The solvent, at least for an oil-soluble active ingredient, preferably has a low relative molecular mass, namely less than about 200.

Suitable compounds include aromatic hydrocarbons, lower alkyl esters, lower ketones, lower alkanols and lower alkanes, the term "lower" meaning C1–12, preferably C1–10 and more preferably C1–8.

Particular solvents include the following, all available from Exxon Chemicals Limited;

"Solvesso 150"—An aromatic hydrocarbon solvent (C9 to C11) with a distillation range 190° to 210° C.

"Solvesso 200"—An aromatic hydrocarbon solvent (C10 to C12) with a distillation range 226° to 290° C.

"Exxate 700"—Heptyl acetate 99% pure, or Odourless kerosene—A mixture of high boiling non-aromatic hydrocarbons consisting of paraffins and naphthenes with a distillation range of 180° to 270° C.

The formulation may comprise more than one pyrethroid (optionally with a synergist or potentiator, which is regarded as an active ingredient for the purpose of the Formula above), more than one solvent, more than one emulsifier and/or more than one stabiliser, together with other ingredients such as perfumes and dyes.

The present invention also provides a method for preventing the resurgance of mite infestation in plants when treated with pyrethroid insecticides which comprises the application to the plant of an aqueous formulation that contains the pyrethroid insecticide as active ingredient, an evaporation retardant and an emulsifier that satisfies the Formula described hereinbefore.

EXAMPLE 1A

A ULV insecticide formulation is made up as follows:

|  | % mass/mass | Rel. molar mass |
|---|---|---|
| Oil phase |  |  |
| Permethrin | 10.32 | 391 |
| S-Bioallethrin | 1.51 | 302 |
| Piperonyl Butoxide | 11.32 | 338 |
| Odourless kerosene | 9.30 | 170 |
| Hexadecan-1-ol | 3.00 | 242 |
| Emulsifiers |  |  |
| Tegoplant EM11 | 0.75 |  |
| Brij 76 | 0.24 |  |
| Tween 20 | 0.01 |  |

-continued

|  | % mass/mass | Rel. molar mass |
|---|---|---|
| Aqueous phase | | |
| Water | 63.45 | 18 |
| Silocolapse 5000 | 0.10 | — |

"Silcolapse" is a Regd. T.M.

The concentrade is diluted 1+9 parts with water for application.

Average relative molar mass of oil phase=271

Molar solubility ratio (moles oil phase/moles alkanol)= 9.4

Model prediction: ratio (mass of oil phase/mass of alkanol) of a formulation within the scope of the invention:

Maximum ratio with an evaporation rate (L) of 15=27.5. with L of 10=17 and with L of 5=7.

Hence, the invention encompasses all such formulations where the mass ratio for this solvent/pesticide mixture to hexadecan-1-ol is less than or equal to 27.

The above formulation has the ratio (mass of oil phase/mass of alkanol)=10.8 and the ratio (moles water/moles of alkanol)=4318 when diluted.

Observed averake evaporation rate (L) =3.8

EXAMPLE 1B

A ULV insecticide spray

|  | % mass/mass | Rel. molar mass |
|---|---|---|
| Oil phase | | |
| Permethrin | 10.87 | 391 |
| S-Bioallethrin | 0.15 | 302 |
| Piperonyl butoxide | 11.07 | 338 |
| Odourless kerosene | 9.30 | 170 |
| Hexadecan-1-ol | 3.00 | 242 |
| Emulsifiers | | |
| Tegoplant EM11 | 0.75 | |
| Brij 76 | 0.24 | |
| Tween 20 | 0.01 | |
| Aqueous phase | | |
| Water | 64.51 | 18 |
| Silcolapse 5000 | 0.10 | |

EXAMPLE 2

A ULV insecticide formulation

|  | % mass/mass | Rel. molar mass |
|---|---|---|
| Oil Phase | | |
| Deltamethrin | 1.0 | 505 |
| Heptyl acetate (Exxate 700) [Exxon Chemicals] | 30.0 | 158 |
| Hexadecan-1-ol | 5.0 | 242 |
| Emulsifier | | |
| Tegoplant EM11 | 1.0 | 800 |
| Aqueous phase | | |

-continued

|  | % mass/mass | Rel. molar mass |
|---|---|---|
| Silicolapse 5000 (anti foam agent) | 0.1 | — |
| Water | 62.9 | 18 |

The concentrate is diluted 1+19 parts with water for spray application.

The parameters for these and the subsequent Examples are given in Table 1.

EXAMPLE 3

A ULV insecticide Formulation

|  | % mass/mass | Rel. molar mass |
|---|---|---|
| Oil Phase | | |
| Alpha cypermethrin | 2.0 | 416 |
| Heptyl acetate (Exxate 700) [Exxon Chemicals] | 30.0 | 158 |
| Hexadecan-1-ol | 7.0 | 242 |
| Emulsifier | | |
| Tegoplant EM11 | 1.0 | 800 |
| Aqueous phase | | |
| Water | 60.0 | 18 |

Observed average evaporation rate =4.5

EXAMPLE 4

A ULV insecticide formulation

|  | % mass/mass | Rel. molar mass |
|---|---|---|
| Oil phase | | |
| Permethrin | 25.0 | 391 |
| 4-methylpentan-2-one | 32.0 | 100 |
| Hexadecan-1-ol | 6.0 | 242 |
| Propan-2-ol | 32.0 | —* |
| Emulsifiers | | |
| Tween 80 | 3.6 | |
| Span 80 | 1.4 | |

*assumed to partition mostly into the aqueous phase on dilution as it is water-miscible.

This formulation was found to be particularly effective.

EXAMPLE 4B

A ULV insecticide spray

|  | % mass/mass | Rel. molar mass |
|---|---|---|
| Oil phase | | |
| Permethrin | 25.0 | 391 |
| Hexadecan-1-ol | 6.0 | 242 |
| Emulsifiers | | |

-continued

|  | % mass/mass | Rel. molar mass |
|---|---|---|
| PMO | 3.6 | |
| SMO | 1.4 | |
| Aqueous phase | None | |

EXAMPLE 5

A pressure packed insecticide formulation

|  | % mass/mass | Rel. molar mass |
|---|---|---|
| Oil phase | | |
| Bioallethrin | 0.315 | 302 |
| Permethrin | 0.038 | 391 |
| Odourless kerosene | 8.3 | 170 |
| Butane | 40.0 | —* |
| Hexadecan-1-ol | 1.0 | 242 |
| Emulsifier | | |
| Tegoplant EM11 | 1.0 | 800 |
| Aqueous phase | | |
| Water | 50.347 | 18 |

*excluded due to its volatility (vapour at normal temperatures and pressures)

EXAMPLE 6

A ULV insecticide formulation

|  | % mass/mass | Rel. molar mass |
|---|---|---|
| Oil phase | | |
| Pyrethrins (PY) | 2.0 | 350 |
| Solvent in PY extract | 6.0 | 150 |
| Piperonyl Butoxide | 16.0 | 338 |
| Octadecan-1-ol | 2.5 | 270 |
| Emulsifier | | |
| Tegoplant EM11 | 1.0 | 800 |
| Aqueous phase | | |
| Water | 72.4 | 18 |
| Silcolapse 5000 | 0.1 | — |

Ready use concentrate (no further dilution required).

EXAMPLE 7

A ULV insecticide formulation

|  | % mass/mass | Rel. molar mass |
|---|---|---|
| Oil phase | | |
| Chlorpyrifos-methyl | 20.0 | 323.0 |
| Solvesso 150 | 20.0 | 144.0 |
| [Exxon Chemicals] | | |
| Hexadecan-1-ol | 3.0 | 242 |
| Emulsifiers | | |
| Tegoplant EM11 | 2.0 | — |

-continued

|  | % mass/mass | Rel. molar mass |
|---|---|---|
| Aqueous phase | | |
| Water | 54.9 | 18 |
| Silcolapse 5000 | 0.1 | |

EXAMPLE 8

A wettable powder formulation

|  | % mass/mass | Rel. molar mass |
|---|---|---|
| Inorganic carrier | | |
| Celite 204 | 64.0 | — |
| Oil phase | | |
| Permethrin | 25.0 | 391 |
| Hexadecan-1-ol | 6.0 | 141 |
| Emulsifiers/dispersing agents | | |
| Tegoplant EM11 | 1.0 | |
| Sodium diisopropyl naphthalene sulphonate e.g. Aerosol OS [Cyanamid G.B. Ltd.] | 4.0 | |

EXAMPLE 9

A ULV herbicide formulation (containing water soluble herbicide).

|  | % mass/mass | Rel. molar mass |
|---|---|---|
| Oil phase | | |
| Solvesso 200 | 10.0 | 163.0 |
| Hexadecan-1-ol | 3.0 | 242 |
| Emulsifiers | | |
| Span 80 | 6.6 | |
| Tween 80 | 3.4 | |
| Aqueous phase | | |
| Water | 40.0 | 18 |
| Glyphosate -mono isopropylammonium | 36.9 | |

This formulation may be modified for other water-miscible active ingredients, for example the components of Bordeaux mixture or quaternary ammonium compounds.

EXAMPLE 10

An LV synergist spray.

|  | % mass/mass | Rel. molar mass |
|---|---|---|
| Oil phase | | |
| Piperonyl butoxide | 64.0 | 338 |
| Hexadecan-1ol | 7.5 | 242 |
| Emulsifiers | | |
| NPE | | 7.0 |

-continued

| | % mass/mass | Rel. molar mass |
|---|---|---|
| Aqueous phase | None | |
| Inert/water soluble ingredients | | |
| Propan-2-ol | 21.5 | |

EXAMPLE 11

An LV insecticide spray.

| | % mass/mass | Rel. molar mass |
|---|---|---|
| Oil phase | | |
| Solvesso 150 | 8.8 | 144 |
| Hexadecan-1-ol | 1.2 | 242 |
| Emulsifiers | | |
| SMO | 0.3 | |
| PMO | 0.9 | |
| Aqueous phase | None | |
| Inert/water soluble ingredients | | |
| Dimethoate | 80.0 | |
| Propan-2-ol | 8.8 | |

EXAMPLE 12

A wettable powder insecticide spray

| | % mass/mass | Rel. molar mass |
|---|---|---|
| Oil phase | | |
| Solvesso 150 | 25.0 | 144 |
| Hexadecan-1-ol | 5.0 | 242 |
| Emulsifiers | | |
| SDNS | 7.5 | |
| Aqueous phase | None | |
| Inert/water soluble ingredients | | |
| Diflubenzuron | 25.0 | |
| Mineral silicates | 37.5 | |

EXAMPLE 13

A flowable fungicide spray

| | % mass/mass | Rel. molar mass |
|---|---|---|
| Oil phase | | |
| Solvesso 150 | 15.0 | 144 |
| Hexadecan-1-ol | 6.0 | 242 |
| Emulsifiers | | |
| SMO | 1.4 | |
| PMO | 3.6 | |
| Aqueous phase | | |
| Water (pH = 13) | 48.9 | 18 |
| Sodium hydroxide | 0.1 | |
| 1,2 propandiol | 4.0 | |

-continued

| | % mass/mass | Rel. molar mass |
|---|---|---|
| Inert/water soluble ingredients | | |
| Thiabendazole | 20.0 | |
| Xanthan gum | 0.5 | |
| Mineral silicates | 0.5 | |

EXAMPLE 14

An LV insecticide spray

| | % mass/mass | Rel. molar mass |
|---|---|---|
| Oil phase | | |
| Exxate 700 | 5.0 | 158 |
| Hexadecan-1-ol | 4.0 | 242 |
| Emulsifiers | | |
| OE/PGO | 2.4 | |
| Aqueous phase | None | |

EXAMPLE 15

A ULV insecticide spray

| | % mass/mass | Rel. molar mass |
|---|---|---|
| Oil phase | | |
| Cypermethrin | 10.0 | 416 |
| Solvesso 150 | 40.0 | 144 |
| Hexadecan-1-ol | 4.0 | 242 |
| Emulsifiers | | |
| OE/PGO | 2.0 | |
| Aqueous phase | | |
| Water | 44.0 | |
| Inert/water soluble ingredients | | |
| | None | |

EXAMPLE 16

A ULV insecticide spray

| | % mass/mass | Rel. molar mass |
|---|---|---|
| Oil phase | | |
| Methoprene | 28.0 | 311 |
| Solvesso 150 | 28.0 | 144 |
| Hexadecan-1-ol | 7.0 | 242 |
| Emulsifiers | | |
| NPE | 4.0 | |
| Aqueous phase | None | |
| Inert/water soluble ingredients | | |
| Propsal-2-ol | 33.0 | |

EXAMPLE 17

An LV insecticide spray

| | % mass/mass | Rel. molar mass |
|---|---|---|
| Oil phase | | |
| Amitraz | 18.0 | 293 |
| Solvesso 150 | 36.0 | 144 |
| 1-Hexadecylamine | 16.3 | 242 |
| Emulsifiers | | |
| SMO | 1.8 | |
| PMO | 4.5 | |
| Aqueous phase | None | |
| Inert/water soluble ingredients | | |
| Propan-2-ol | 23.4 | |

EXAMPLE 18

An LV insecticide spray

| | % mass/mass | Rel. molar mass |
|---|---|---|
| Oil phase | | |
| Malathion | 65.0 | 330 |
| Hexadecan-1-ol | 7.5 | 242 |
| Emulsifiers | | |
| SMO | 2.0 | |
| PMO | 5.0 | |
| Aqueous phase | None | |
| Inert/water soluble ingredients | | |
| Propan-2-ol | 20.5 | |

EXAMPLE 19

An LV insecticide spray

| | % mass/mass | Rel. molar mass |
|---|---|---|
| Oil phase | | |
| Fenitrothion | 65.0 | 277 |
| Hexadecan-1-ol | 4.0 | 242 |
| Emulsifiers | | |
| SMO | 2.0 | |
| PMO | 5.0 | |
| Aqueous phase | None | |
| Inert/water soluble ingredients | | |
| Propan-2-ol | 24.0 | |

Comparative Example A (A ULV insecticide formation)*

| Oil phase | % mass/mass | Rel. molar mass |
|---|---|---|
| Permethrin | 10.8 | 391 |
| S-Bioallethrin | 1.7 | 302 |

| Oil phase | % mass/mass | Rel. molar mass |
|---|---|---|
| Piperonyl Butoxide | 12.3 | 338 |
| Mineral oil | 20.0 | 296 |
| Kerosene | 41.7 | 170 |
| Hexadecan-1-ol | 1.0 | 242 |
| Nonylphenol ethylene oxide condensate** | 8.2 | 638 |
| Calcium dodecyl benzenesulphonate** | 4.3 | 394 |

**emulsifiers assumed to partition mostly into aqueous phase on dilution.

Dilute 1+9 with water for application.

Average relative molar mass of oil phase=254

Molar solubility ratio (moles oil phase/moles long chain alcohol)=10.0

Model prediction ratio {mass of oil phase/mass of alkanol) of a formulation within the scope of the invention:

Maximum ratio with an evaporation rate (L) of 15 units= 33.0, with an L of 10 units=20.4, and with an L of 5 units=9.0

The above formulation has the ratio (moles of oil phase/ moles long chain alcohol)=86, and is therefore outside the scope of the invention.

The ratio (moles of water/moles of alkanol)=12100 on dilution.

Observed average evaporation rate=20 units

*Example 1 of GB-A-2 095 109.

ANALYSIS OF FORMULATIONS

The analysis of a given formulation to determine whther it satisfies the formula above is illustrated as follows.

Analysis of Example 1A

The permethrin, S-bioallethrin, piperonyl butoxide, odourless kerosene, emulsifiers and antifoam agent could constitute the oil phase. Each one of these components may be taken in turn at the level in the formulation and diluted in water (%1+9). Onr would observe that the permethrin, S-bioallethrin, odourless kerosene and piperonyl butoxide are not miscible with water at this dilution level, eg. permethrin has a solubility of 0.2 mg/l of water at 30° C. These components would therefore constitute the oil phase. The emulsifiers would be miscible with water giving a clear solution upon dilution. Of the antifoam agent, (o.1%) 30% of this would not be soluble in the oil phase or the water and would simply be classed as an inert ingredient. The oil phase would then be constituted in the proportions in the formulation. The solubility limit of hexadecan-1-ol would be determined by preparing s series of mixtures and noting the maximum composition at which all the hexadecan-1-ol remained in solution at 27° C. after a period of 24 hours. A mixture containing 8.7% mass/mass of hexadecan-1-ol is the composition in this case. The relative molar mass of the oil phase is also required. This is calculated as follows from the relative molar mass of each component and the proportions in the oil phase:

$$\frac{10.32}{391} + \frac{1.51}{302} + \frac{11.32}{338} + \frac{9.30}{170} = \frac{32.45}{RMM \text{ mixture}}$$

RMM mixture=271

The relative molar mass of hexadecan-1-ol is 242.

The molar solubility ratio (moles oil phase/moles film forming agent)

=((100−8.7)/271)/(8.7/242)=9.37

This provides all the variables to use in the right hand side of the equation. With L=15 the predicted maximum ratio of mass of oil phase to film forming agent is 27. The above formulation has a mass of oil phase to film forming agent of 10.8 (33.45/3). Therefore it is clearly within the scope of the formula. The level of hexadecan-1-ol could be reduced to 1.21% with the same level of oil phase and still remain within the cope of the formula. However, a formulation with 1.0% hexadecan-1-ol would be outside the scope of the formula.

Analysis of Example 4A

This formulation contains permethrin, 4-methylpentan-2-one, hexadecan-1-ol, emulsifiers and propan-2-ol. The formulation is diluted 1+9 parts with water for use.

All the components given could potentially constitute the oil phase once diluted. Propan-2-ol is completely miscible with water over all compositions. The emulsifiers are also water miscible when diluted. The permethrin and 4-methyl pentan-2-one are not completely miscible with water when diluted at this level. The oil phase therefore consists of permethrin and 4-methyl-pentan-2-one. The solubility of hexadecan-1-ol is determined in this mixture as described above at 27° C. The solubility of hexadecan-1-ol in the mixture of permethrin and 4-methylpentan-2-one is 16.0% mass/mass. The relative molar mass of the oil phase is calculated from the relative molar mass of the components and their proportion in the oil phase:

$$\frac{25.0}{391} + \frac{32.0}{100} = \frac{87.0}{RMM\ \text{mixture}}$$

RMM mixture=149

The relative molar mass of hexadecan-1-ol is 242.

The molar solubility ratio (moles oil phase/moles film forming agent)

=([100−16.1])/149)/(16/242)=8.5

This gives all the variables to be used on the right hand side of the equation. With L=15 then the maximum ratio of oil phase to hexadecan-1-ol is 66. The above formulation has a mass ratio of oil phase to film-forming anent of 9.5 and is therefore well within the scope of the formula. The level of hexadecan-1-ol could be reduced to 0.87% whilst maintaining the oil phase levels constant and still remain within the scope of the formula.

Analysis of Example 4B

It will be observed that this formulation is the same as that given as example 4A except that the formulation is ddiluted 1+29 parts with water. Permethrin is the only component within the formulation that is immiscible with water at this level of dilution. 0.32 g of 4-methyl-pentan- 2-one dissolves completely in 29 g of water. The permethrin in this example constitutes the oil phase. The solubility of hexadecan-1-ol in permethrin is 1.8% w/w which gives a molar solubility ratio of 33.7.

With L=15 the maximum ratio of oil phase to film-forming agent is 99. At this dilution level the level of hexadecan-1-ol in the formulation could be reduced to 0.4% and still remain within the scope of the formula. This also provided an example of where the evaporation rate of a formulation is improved as a result of further dilution because of additional partitioning of one of the oil phase components in the aqueous phase. There is less oil phase for the film forming agent to dissolve in, thus more will be available to form a film at the surface of the droplet.

Analysis of Example 13

This formulation contains Solvesso 150, hexadecan-1-ol, emulsifiers, water, sodium hydroxide, 1,2-propandiol, thiabendazole, xanthan gum, and mineral silicates. This is a fairly complex formulation. The active ingredient is not particularly soluble in the aqueous or oil phase. A fine particulate suspension of the active ingredient is therefore made. The formulation also contains a thickening agent to aid the suspension of the particulates. This is a high molecular weight polysaccharide that is insoluble in the oil phase and can be regarded as an inert substance. The formulation also contains powered mineral silicates of low bulk density to prevent the formulation "caking" (particles sticking together). The 1,2-propandiol is added to prevent freezing and is completely water miscible. The sodium hydroxide is added to buffer the formulation at around pH13 and is water soluble. The oil phase therefore consists of only Solvesso 150 with possibly a small amount of thiabendazole dissolved in it.

The solubility of hexadecan-1-ol in Solvesso 150 is 23.5% mass/mass. The relative molar mass of Solvesso 150 is 144. The molar solubility is 5.5.

The right hand side of the formula with L=15, gives a ratio mass of oil phase/mass of film forming agent)+35. The formulation has a mass ratio of 2.5 and is The solubility of hexadecan-1-ol in Solvesso 150 is 23.5% mass/mass. The relative molar mass of Solvesso 150 is 144. The molar solubility is 5.5.

The right hand side of the formula with L=15, gives a ratio (mass of oil phase/mass of film forming agent)= 35. The formulation has a mass ratio of 2.5 and is clearly within the scope of the formula. The level of hexadecan-1-ol could be reduced substantially and the formulation would remain within the scope of the formula.

TABLE 1

| Example No: | 1A | 1B | 2 | 3 | 4A | 4B |
| --- | --- | --- | --- | --- | --- | --- |
| Dilution for appln. 1 + n | 9 | 9 | 19 | 29 | 9 | 29 |
| Av. Rel. Molar mass of oil phase | 271 | 271 | 162 | 164 | 149 | 391 |
| Mass solubility | 8.7 | 8.7 | 16.5 | 16.5 | 16.0 | 1.8 |
| Molar solubility ratio | 9.4 | 9.4 | 7.6 | 7.5 | 8.5 | 33.7 |
| Maximum ratio calcd. for L | | | | | | |
| L = 15 | 27 | 27 | 47 | 45 | 66 | 99 |
| L = 10 | 17 | 17 | 29 | 28 | 41 | 61 |
| L = 5 | 7 | 7 | 13 | 12 | 18 | 27 |
| Mass of oil | | | | | | |
| Mass of film-former | 10.8 | 10.5 | 6.2 | 4.6 | 9.5 | 9.5 |
| L measured Moles (water) | 3.8 | 3.8 | 4.0 | 4.5 | 5.0 | 4.2 |

TABLE 1-continued

| Moles (film-former) | 4318 | 5278 | 5278 | 5683 | 2016 | 6498 |
|---|---|---|---|---|---|---|
| Example No: | 5 | 6 | 7 | 8 | 9 | |
| Dilution for appln. 1 + n | 0 | 0 | 14 | 39 | 39 | |
| Av. Rel. Molar mass of oil phase | 173 | 258 | 199 | 391 | 153 | |
| Mass solubility | 7.5 | 4.0 | 9.0 | 1.8 | 12.5 | |
| Molar solubility ratio Maximum ratio calcd. for L | 17.2 | 25.1 | 12.2 | 33.7 | 10.4 | |
| L = 15 | 145 | 116 | 68 | 99 | 75 | |
| L = 10 | 90 | 72 | 42 | 61 | 47 | |
| L = 5 | 40 | 32 | 19 | 99 | 21 | |
| Mass of oil | | | | | | |
| Mass of film-former | 8.6 | 9.6 | 13.3 | 8.5 | 8.5 | |
| L measured Moles (water) | 3.8 | 4.8 | 4.7 | 5.3 | 3.8 | |
| Moles (film-former) | 663 | 435 | 6520 | 6691 | 32490 | |
| Example No: | 10 | 11 | 12 | 13 | 14 | |
| Dilution for appln. 1 + n | 39 | 29 | 39 | 49 | 19 | |
| Av. Rel. Molar mass of oil phase | 338 | 144 | 144 | 144 | 158 | |
| Mass solubility | 5.5 | 23.5 | 23.5 | 23.5 | 16.5 | |
| Molar solubility ratio Maximum ratio calcd. for L | 12.3 | 5.5 | 5.5 | 5.5 | 7.8 | |
| L = 15 | 28 | 35 | 35 | 35 | 51 | |
| L = 10 | 17 | 22 | 22 | 22 | 32 | |
| L = 5 | 8 | 10 | 10 | 10 | 14 | |
| Mass of oil | | | | | | |
| Mass of film-former | 5.0 | 2.5 | 5.0 | 2.5 | 1.3 | |
| L measured Moles (water) | 5.3 | 7.5 | 7.0 | 7.5 | 7.3 | |
| Moles (film-former) | 6991 | 11089 | 10487 | 11089 | 9747 | |
| Example No: | 15 | 16 | 17 | 18 | 19 | |
| Dilution for appln. 1 + n | 19 | 19 | 19 | 19 | 19 | |
| Av. Rel. Molar mass of oil phase | 166 | 197 | 173 | 330 | 277 | |
| Mass solubility | 15.0 | 18.5 | 20.1 | 1.9 | 0.8 | |
| Molar solubility ratio Maximum ratio calcd. for L | 8.2 | 5.4 | 5.5 | 37.8 | 108 | |
| L = 15 | 52 | 20 | 26 | 157 | 1038 | |
| L = 10 | 32 | 13 | 16 | 97 | 643 | |
| L = 5 | 14 | 6 | 7 | 43 | 284 | |
| Mass of oil | | | | | | |
| Mass of film-former | 12.5 | 8.0 | 3.3 | 8.7 | 16.3 | |
| L measured Moles (water) | 4.7 | 7.8 | 4.5 | 6.4 | 5.1 | |
| Moles (film-former) | 6534 | 3649 | 1567 | 3402 | 6386 | |

The following examples illustrate representative formulations to be applied and the biological properties of such formulations:

EXAMPLE 20

Formulation 1

| Ingredient | % w/w |
|---|---|
| Permethrin (Technical) | 10.32 |
| Piperonyl Butoxide (Technical) | 12.83 |
| Cetyl Alcohol | 3.00 |
| Odourless Kerosene | 9.70 |
| Emulsifier Blend | 1.00 |
| Deionised Water | 62.75 |
| Silcolapse 5000 | 0.10 |
| Formaldehyde Solution | 0.30 |
| | 100.00 |

1% Emulsifier Blend consists of 0.75% Emulgator BT02, 0.1% BRIJ 78, 0.1% BRIJ 72 and 0.05% TWEEN20.

Emulgator BT02 is equivalent to Tegoplant EM11 described in European Patent 331474.

Biological Properties 1501 m Diameter droplets of Ambush™ (which is a formulation marketed by ICI Americas Inc) and formulation 1 were applied to 2 cm diameter leaf discs cut from "Henderson" lima beans. Both formulations were mixed in water at a rate of 12.5 g a.i. per liter.

Droplets were applied at densities of 25, 50, 75, 100, 150 and 200 per leaf disc. Five replicate leaf discs were used per droplet density. Five replicate control leaf discs were left untreated.

Leaf discs were left to dry for one hour. Five adult female two-spotted spider mites (TSSM) were then placed on each leaft disc using a fine camel-hair brush. The mites were obtained from cultures reared on greenhouse lima beans at the OARDC. The leaf discs were placed on moistened cotton in 3 cm diameter petri dishes and were maintained in the laboratory at room temperature (22°–25° C.).

At 24 and 48 hours following treatment, the following were assessed: mortality, the number of mites on and off the leaf disc, the number of eggs and the number of feeding scars. Mites were recorded as dead when they would not respond to gentle prodding.

For each parameter measured the data were analysed using a one-way analysis of variance. Significant treatment effects were partitioned using a Student-Newman-Keuls (SNK) multiple range test. Prior to analyses, the data were first transformed using either percentages and arcsin-square-root (mortality, irritancy) or $\log_{10} n+1$ (eggs/mite, scars/mite). The effects of droplet density upon the parameters measured were then subsequently analysed using linear regression analyses.

The individual treatment means and the results of the SNK multiple range test were plotted for irritancy, fecundity and feeding rate at 24 hours after exposure. Significant treatment effects were detected in the measurements of irritancy, fecundity and feeding rate but not in the measurement of mortality. In all, very few mites died throughout the study, in any of the treatments. This was expected as the rates of permethrin that were chosen were selected in order to investigate the sub-lethal effects of these pesticides upon TSSM.

For all the parameters measured, no treatment effects were detected for formulation 1. However, significant treatment effects were detected with Ambush.

By increasing the droplet density, it was observed with Ambush, a significant increase in the number of TSSM leaving the leaf, which took place concomitant with a significant decrease in the number of eggs laid and the amount of feeding activity (despite a correction for the number of TSSM that remained on the leaf).

What is claimed is:

1. A formulation suitable for spraying or for dilution with water to form a sprayable preparation, the formulation consisting essentially of an active ingredient, an emulsifier and an evaporation retardant, wherein the formulation satisfies the following formula:

$$\frac{\text{mass of oil phase}}{\text{mass of retardant}} \leq \frac{M_{oil}}{M_{retardant}} \times \text{Exp} \frac{\ln(L/4) + C\ln(AX^B)}{C}$$

where L is less than or equal to 15, A=700376, B=−1.51, C=0.8472, the oil phase is the liquid non-aqueous phase containing the active ingredient, solvent if present and the emulsifier, provided those components are not miscible with water at the dilution level employed, $M_{oil}$ is the weighted average relative molar mass of the oil phase, $M_{retardant}$ is the weighted average relative molar mass of the retardant, and $$X = \frac{(M_{oil})^{1.8}}{Y}$$

where Y is the molar solubility ratio of the formulation, defined as the minimum number of moles of the oil phase which will dissolve the retardant, divided by the number of moles of retardant, provided that, in the Formula above, any solvent which has no liquid phase at 27° C. at atmospheric pressure is excluded, and wherein the active ingredient is sprayable in a water-based formulation and is an insecticide, acaricide, herbicide, fungicide, plant growth regulator, insect behavior modifier, biological control agent, dye, perfume, bactericide, lubricant, medicament, paint, polish, lacquer or textile treatment, the emulsifier is an anionic compound, a cationic compound, a nonionic compound or mixtures thereof having a hydrophilic/lipophilic balance of 8 to 18, and the evaporation retardant is a $C_{16-20}$ alkanol, 1-hexadecylamine, 1-heptadecylamine or 1-octadecylamine and wherein the formulation optionally also contains a carrier or solvent for the active ingredient.

2. A formulation according to claim 1 wherein L is less than 10.

3. A formulation according to claim 2 wherein L is less than 5.

4. A formulation according to claim 1 wherein the active ingredient is a pesticide or herbicide.

5. A formulation according to claim 4 wherein the active ingredient is a pyrethroid.

6. A formulation according to claim 1 wherein the solvent has a relative molar mass of less than 200.

7. A formulation according to claim 6 wherein the solvent comprises kerosene, odorless kerosene, mineral oil, heptyl acetate, 4-methylpentan-2-one or butane.

8. A formulation according to claim 1 wherein the formulation is an ultra-low volume concentrate and the proportion of the oil phase is between 8% and 30% by mass before dilution for use.

9. A formulation according to claim 1 wherein the formulation is a wettable power.

10. A formulation according to claim 1 wherein the evaporation retardant is hexadecan-1-ol or a mixture of hexadecan-1-ol and octadecan-1-ol.

11. A formulation according to claim 10 which is to be diluted before use and which comprises more than 1.0 to 7.5% evaporation retardant by mass.

12. A formulation according to claim 1 wherein the emulsifier is a non-ionic compound with an HLB value of 8–18, or a mixture of non-ionic compounds, the mixture having a weighted average HLB value of 8–18.

13. A formulation according to claim 1 which is diluted and ready for use and which comprises 0.0 to 3.2% oil phase by weight.

14. A formulation according to claim 13 which is diluted and ready for use and which comprises 0.25 to 1.5% oil phase by weight.

15. A method of combating insect or acarine pests or unwanted plants by spraying a formulation according to claim 1, optionally diluted with water, wherein the formulation comprises an insecticide, acaricide or herbicide.

16. A method of controlling insects on plants which comprises applying to the plant an effective amount of an aqueous formulation that consists essentially of a pyrethroid insecticide as an active ingredient, an evaporation retardant and an emulsifier, which formulation satisfies the formula:

$$\frac{\text{mass of oil phase}}{\text{mass of retardant}} \leq \frac{M_{oil}}{M_{retardant}} \times \text{Exp} \frac{\ln(L/4) + C\ln(AX^B)}{C}$$

where L is less than or equal to 15, A=700376, B=1.51, C=0.8472, $M_{oil}$ is the weighted average relative molar mass of the oil phase $M_{retardant}$ is the average molar mass of the retardant, and $$X = \frac{(M_{oil})^{1.8}}{Y}$$

where Y is the molar solubility ratio of the formulation, defined as the minimum number of moles of oil phase which will dissolve the retardant, divided by the number of moles of retardant, provided that, in the Formula above, any solvent which has no liquid phase at 27° C. at atmospheric pressure is excluded, and wherein the active ingredient is sprayable in a water-based formulation and is an insecticide, acaricide, herbicide, fungicide, plant growth regulator, insect behavior modifier, biological control agent, dye, perfume, bactericide, lubricant, medicament, paint, polish, lacquer or textile treatment, the emulsifier is an anionic compound, a cationic compound, a nonionic compound or mixtures thereof having a hydrophilic/lipophilic balance of 8 to 18, and the evaporation retardant is a $C_{16-20}$ alkanol, 1-hexadecylamine, 1-heptadecylamine or 1-octadecylamine and wherein the formulation optionally also contains a carrier or solvent for the active ingredient.

17. A method for preventing the resurgence of mite infestation in a plant when treated with pyrethroid insecticides which comprises the application to the plant of an effective amount of a formulation as defined in claim 16.

18. A method as claimed in claim 16 in which the formulation optionally comprises more than one pyrethroid optionally with a synergist or potentiator, which is regarded as an active ingredient for the purpose of the formula in claim 16, and/or more than one solvent, and/or more than one emulsifier and/or more than one retardant, optionally together with other ingredients selected from perfumes and dyes.

19. A method as claimed in claim 16 in which the pyrethroid insecticides are either (a) a compound of formula (I)

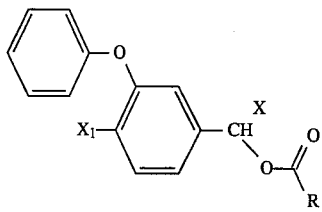

wherein R represents

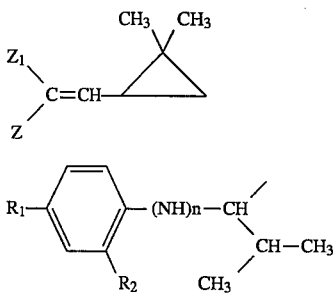

in which $R_1$ is halo, $CF_3$ or $CHF_2O$, $R_2$ represents hydrogen or halo, n is 0 or 1, and Z and $Z_1$ are each independently selected from halo, $CF_3$ and methyl; or $Z(Z_1)C=$ represents:

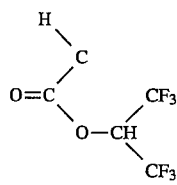

X represents hydrogen or halo, and X is H, CN or $C\equiv CH$, in the form or individual isomers or mixtures thereof; or (b) a compound of formula:

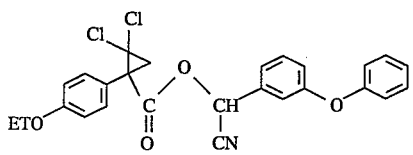

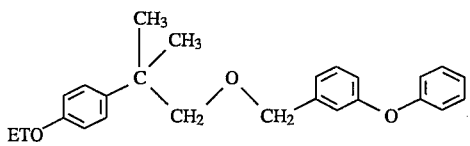

in the form of individual isomers ir mixtures thereof; or (c) a compound selected from flumethrin, bifenthrin, bioallethrin, S-bioallethrin, esbiothrin, resmethrin, bioremesthrin and acrinathrin.

20. A method as claimed in claim 16 wherein L is less than 10.

21. A method as claimed in claim 5 wherein L is less than 5.

22. A method as claimed in claim 16 wherein the amount of emulsifier present in the formulation is less than twice the amount of the evaporation retardant present.

23. A method as claimed in claim 22 wherein the amount of emulsifier present in the formulation is less than the amount of the evaporation retardant present.

24. A method as claimed in claim 16 wherein the emulsifier is a non-ionic compound with an HLB (hydrophilic/ lipophilic balance) value of 8–18, or a mixture of non-ionic compounds, the mixture having a weighted average HLB value of 8–18.

25. A method as claimed in claim 16 wherein the evaporation retardant is hexadecan-1-ol, octadecan-1-ol, octadecan-1-ol or a mixture thereof.

* * * * *